(12) United States Patent
Bitoun et al.

(10) Patent No.: US 10,587,545 B1
(45) Date of Patent: Mar. 10, 2020

(54) WEB-BASED SYSTEM FOR ENHANCING USER WELL-BEING

(71) Applicant: SAGELY, INC., Honolulu, HI (US)

(72) Inventors: Alex Bitoun, Haiku, HI (US); Warren Wong, Honolulu, HI (US); Julie Jolene Green, Honolulu, HI (US); Martin Ryssen, Marcq-en-Baroeul (FR); Gabriel Lasne, Melun (FR)

(73) Assignee: Sagely, Inc., Honolulu, HI (US)

( * ) Notice: Subject to any disclaimer, the term of this patent is extended or adjusted under 35 U.S.C. 154(b) by 0 days.

(21) Appl. No.: 16/362,632

(22) Filed: Mar. 23, 2019

(51) Int. Cl.
*H04L 12/58* (2006.01)
*G06F 16/9535* (2019.01)
*H04L 29/08* (2006.01)

(52) U.S. Cl.
CPC ........ *H04L 51/063* (2013.01); *G06F 16/9535* (2019.01); *H04L 51/02* (2013.01); *H04L 51/046* (2013.01); *H04L 67/22* (2013.01)

(58) Field of Classification Search
CPC ............. G06F 19/3418; G06F 16/9535; H04L 51/063; H04L 67/22; H04L 51/046; H04L 51/02
See application file for complete search history.

(56) References Cited

U.S. PATENT DOCUMENTS

| | | | | |
|---|---|---|---|---|
| 7,953,613 B2* | 5/2011 | Gizewski | ............ | G06F 19/3456 705/3 |
| 8,010,400 B2* | 8/2011 | Mascarenhas | ......... | G06Q 30/02 705/7.29 |
| 8,676,607 B2* | 3/2014 | Patel | ...................... | G06Q 50/22 705/3 |
| 9,734,290 B2* | 8/2017 | Srinivas | ................. | G06Q 40/08 |
| 9,848,061 B1* | 12/2017 | Jain | ..................... | G06F 3/04847 |
| 9,898,789 B2* | 2/2018 | Ram | ...................... | G06Q 50/24 |
| 10,325,070 B2* | 6/2019 | Beale | .................. | G06F 19/3418 |
| 10,412,210 B2* | 9/2019 | Bjontegard | ........... | A63F 13/216 |
| 2005/0228692 A1* | 10/2005 | Hodgdon | ............... | G06Q 30/02 705/2 |

(Continued)

OTHER PUBLICATIONS

Bland, J. Martin, and Douglas G. Altman. "Statistics notes: Cronbach's alpha." Bmj 314.7080 (1997): 572.*

(Continued)

*Primary Examiner* — Jimmy H Tran
(74) *Attorney, Agent, or Firm* — Eric P. Mirabel, JD, LLM (57) ABSTRACT

The invention relates to a method of improving a user's well-being in an interactive system, by: querying the user to determine a user identifier profile and the user's relative levels of a number of state-related traits, and identifying traits for which said relative levels deviate significantly from optimal; wherein the improvement includes: selecting, by a server, from a group of tested motivational messages which have been effective for other users to reduce the deviation in the levels of said traits, one or more selected motivational messages; where the amount of said deviation reduction is the average of all users reduction in deviation following receipt of said selected motivational messages; and sending the selected motivational messages to the device controlled by the user; and querying the user, by sending a questionnaire from the server to said device, to determine if said deviation is reduced.

9 Claims, 4 Drawing Sheets

(56) References Cited

U.S. PATENT DOCUMENTS

| | | | |
|---|---|---|---|
| 2006/0200368 A1* | 9/2006 | Casey | G06Q 50/24 705/3 |
| 2007/0033084 A1* | 2/2007 | Mascarenhas | G06Q 30/02 705/7.33 |
| 2007/0111176 A1* | 5/2007 | Brown | G06Q 10/10 434/262 |
| 2007/0122780 A1* | 5/2007 | Moon | G09B 5/00 434/236 |
| 2008/0197185 A1* | 8/2008 | Cronin | G06F 19/328 235/375 |
| 2008/0227063 A1* | 9/2008 | Kenedy | G06F 16/951 434/219 |
| 2009/0106004 A1* | 4/2009 | Edwards | G06F 19/00 703/6 |
| 2010/0138232 A1* | 6/2010 | Ryan | G06Q 40/08 705/2 |
| 2011/0230732 A1* | 9/2011 | Edman | A61B 5/4869 600/301 |
| 2012/0041801 A1* | 2/2012 | Mascarenhas | G06Q 30/02 705/7.32 |
| 2012/0179480 A1* | 7/2012 | Patel | G06Q 50/22 705/2 |
| 2012/0185266 A1* | 7/2012 | Trifunov | G06Q 50/22 705/2 |
| 2013/0101970 A1* | 4/2013 | Mascarenhas | G09B 19/00 434/236 |
| 2013/0226614 A1* | 8/2013 | Bustani | G06F 19/324 705/3 |
| 2013/0291060 A1* | 10/2013 | Moore | G06F 21/6245 726/1 |
| 2014/0214709 A1* | 7/2014 | Greaney | G06Q 10/1053 705/321 |
| 2014/0278474 A1* | 9/2014 | McClure | G06F 19/3418 705/2 |
| 2014/0310013 A1* | 10/2014 | Ram | G06Q 50/24 705/2 |
| 2014/0372133 A1* | 12/2014 | Austrum | G06F 19/3475 705/2 |
| 2015/0262498 A1* | 9/2015 | Wicka | G06Q 50/22 705/14.27 |
| 2016/0110523 A1* | 4/2016 | Francois | G06Q 50/24 705/2 |
| 2016/0117937 A1* | 4/2016 | Penders | G06F 16/9535 434/236 |
| 2016/0365006 A1* | 12/2016 | Minturn | G09B 5/00 |
| 2017/0031449 A1* | 2/2017 | Karsten | G06F 19/3418 |
| 2017/0039590 A1* | 2/2017 | Moran | G06Q 30/0244 |
| 2017/0300643 A1* | 10/2017 | Bezark | G06F 19/3481 |
| 2017/0309197 A1* | 10/2017 | Spiegel | G06Q 90/00 |
| 2018/0278462 A1* | 9/2018 | Bjontegard | A63F 13/32 |
| 2018/0288213 A1* | 10/2018 | Bjontegard | A63F 13/217 |
| 2018/0375807 A1* | 12/2018 | Krans | H04L 51/046 |
| 2019/0065597 A1* | 2/2019 | Murray | G06F 16/9535 |
| 2019/0088159 A1* | 3/2019 | Minturn | G16H 50/30 |

OTHER PUBLICATIONS

Tavakol, Mohsen, and Reg Dennick. "Making sense of Cronbach's alpha." International journal of medical education 2 (2011): 53.*

Santos, J. Reynaldo A. "Cronbach's alpha: A tool for assessing the reliability of scales." Journal of extension 37.2 (1999): 1-5.*

* cited by examiner

WEB-BASED SYSTEM FOR ENHANCING USER WELL-BEING

BACKGROUND

Well-being is the state of mind of how an individual is feeling. It varies constantly; and thus short term fluctuations are ignored for the purposes of defining a universal measure to assess well-being.

Well-being and wellness encompass managing a disease and changing behaviors to reduce negative behaviors and increase positives. The current health and well-being care system fails to recognize that each patient is on a journey, with multiple challenges which make health and well-being harder to attain. To focus on paths to well-being, not just disease management, leads to better choices, and healthier outcomes.

Well-being is made up of domains: physical, social, mental, environmental and emotional. Each domain is made up of traits, which can be measured by a graded questionnaire. Better understanding of people's traits (which vary over time, and thus, the trait at any particular time are designated a "state"), habits, natural tendencies, and life challenges; and the motivators which help people correct for negative traits and overcome challenges, will aid them in achieving long term health and happiness.

As a general rule, the quantity of difference (or Δ) between any particular subject's state and the desired trait, is the primary motivator for that state or trait. For example, simply losing adipose tissue is generally the primary motivator for an obese subject, but other motivators which are related include: increased social interaction, better relationships, increased happiness, and others.

The well-being state and traits are personal, and differ across a population. The individual motivators which lead to improvements in the states and traits are similarly highly personal. These might include, for example: "I want to be a good role model for my children" or, "I want to be able to care for myself and not be dependent on other people." The first step in finding a method to improve well-being requires finding the personalized states and traits, and the motivators to improve them, where needed.

Well-being state can be determined using a questionnaire approach, where domains and traits, and personalized motivators, are determined by responses to questions. Well-being state can be changed in a positive direction by motivators, and by personal motivators which focus on what motivates the particular individual. AI Deep Learning can be used to analyze traits and challenges across a broad population and determine when intervention in the form of messaging motivators is needed, and can be used to aid in selection of the motivator messages. An interactive system which provides tailored motivational messages for users, is clearly desirable.

SUMMARY

The invention relates to a web-based interactive system, where one first determines (in a personalized manner) each of the members domains and traits/states, and then determines the personalized motivators to improve them in a desired manner. The system allows input from user's devices (smart phones, tablets, PCs, desktops) to a website and server run by an operator; where the server identifies the user and then permits entry by the user of the user's data or responses to messages and questionnaires; and, user's data or responses to messages and questionnaires is analyzed against the user's existing information on the server and preferably that of other users, more preferably using deep learning in such multi-party data analysis, to establish a well-being profile for the user, and then, to provide messages directing the user regarding how to maintain or desirably, positively move the status of each of the traits within their well-being profile.

The invention includes the linkage and interaction of the program or application on a user's device with the server, over the internet and through a website associated with the server. The invention also includes generating a change in the operation of both the server and the user's device through such linkage and interaction.

Diagnosis, which is the first step, requires the user to complete a detailed questionnaire, with graded levels of responses, to determine the user's state in each domain, and the level of each of a number of traits (e.g., mobility, extroversion, purpose) where each state/trait is associated with both general and personalized motivators (e.g., user's need for respectively: autonomy, relation and goals), and where the motivators can be applied to the user through messaging, and where the messages are selected and refined first, in accordance with the user's likely response to a UserMotivator Message, and then further refined based on the user's actual responses to particular UserMotivator Messages.

Table I below shows some major domains, and the states/traits with their associated motivators, and provides the guidelines for the sort of information queried on the questionnaire and then gathered for analysis:

TABLE I

| DOMAIN & Sub-Domain | USER STATE/TRAIT | DEFINITION | MOTIVATOR | CONDITIONS AFFECTING |
|---|---|---|---|---|
| PHYSICAL - Health & Functional | Health (Condition) | The extent to which the member is in a good shape and feels healthy - A low Health Condition might result from illness, malnutrition, low sleep quality or drug interference, making the member | (Need for) Energy - The extent to which the member seeks to gain in vitality, vigor or stamina. | Affected by: Physical well-being; Nutrition; Drug therapy; Environment; Exercise; Rest/sleep |

TABLE I-continued

| DOMAIN & Sub-Domain | USER STATE/TRAIT | DEFINITION | MOTIVATOR | CONDITIONS AFFECTING |
|---|---|---|---|---|
| | | typically feel in pain and exhausted. | | |
| | Functional (Status) | The extent to which the member has good freedom of movement and action - A low Functional Status might result from a loss of autonomy due to physical or mental impairments, making the member feel restrained | (Need for) Mobility - The extent to which the member seeks to gain in freedom of action and physical autonomy. | Affected by: Mobility, Independence, Physical Activity, Self-Determination, Autonomy (e.g., ability to cook, clean, get dressed); Physical ability and Mental state |
| SOCIAL - Connectedness & Interaction Levels | Connectedness/ Socialization level | The number of interactions with many people on a regular basis; able to connect easily with others? A low Socialization Level might lead the member to typically feel lonely, or even abandoned. | (Need for) Social interactions - The extent to which the member seeks to have more social contacts | Affected by: Extroversion (Extraversion; Empathy) Support, Love & Relationships, Family, Friends, Companion Animals, Sense of purpose - requires being recognized for doing good |
| | Interaction level - Moral support | The extent to which the member has a high-level, understanding nature of interaction with friends or family - A low Moral Support from relatives might lead the member to feel typically misunderstood, despite being eventually surrounded by people. | (Need for) Meaningful Relationships - The extent to which the member seeks to develop deeper relationships, at least with a select few people, be it friends or family. | Affected by: Ability to continue with old love and expand love; Forge new relationships; Improve relationships |
| SENSE OF SELF - Dignity & Purpose | Self-Esteem - | The extent to which the member has confidence in [him/her]self in front of others and feels respected by others, making [him/her] believe in their own abilities and capabilities - A low Self-Esteem might result from very demanding and ungrateful environmental conditions, making the member feel | (Need for) Recognition - The extent to which the member needs to be acknowledged by others for [his/her] own efforts and accomplishments, in order to gain self-confidence. | Affected by: Social pressure; Autonomy Achievement; Mastery; Respect |

TABLE I-continued

| DOMAIN & Sub-Domain | USER STATE/TRAIT | DEFINITION | MOTIVATOR | CONDITIONS AFFECTING |
|---|---|---|---|---|
| | | either unworthy or used by others. | | |
| | Purpose (Sense of Achievement) | The extent to which the member plans activities and sets clear goals on a daily basis, towards achieving wider, meaningful purposes for [his/her] life - A low Sense of Achievement might result from depression, making the member feel typically useless. | (Need for) Significant Goals - The extent to which the member seeks to set and take up personal challenges, and achieve more meaningful goals for [his/her] life. | Affected by personal balance of Control-Chaos; different in a Planner vs Non-planner; Conscientiousness; Cognition |
| ENVIRONMENT Entertainment & Resources | Entertainment - Life Enjoyment | The extent to which the member experiences intellectual stimulation, and feels in harmony with [his/her] environment and surroundings - A low Life Enjoyment might result from depression, making the member feel typically bored of everything. | (Need for) Fun; The extent to which the member wishes to have new and/or exciting experiences on a regular basis | Affected by: Enjoying life; New experiences; Learning; Purpose; Surroundings; Explore Talents; Creativity; Fulfillment |
| | Life and Financial Stability | The extent to which the member has reliable living conditions, as well as sufficient financial and tangible resources for [him/her]self - A low Life Stability might result from a global situation of poverty, the loss of a job, or from constant changes in living places, making the member feel typically deprived | (Need for) Security - The extent to which the member needs to feel safer and to have more backup resources in [his/her] life. | Affected by: Lack of resources, Financial stability, Contentment, Income, Expenses, Anxiety |
| | Physiological | | (Need for) Sustenance | Most affected by: Food; Water; Shelter |
| EMOTIONAL - Optimism & Emotional Stability | Optimism | The extent to which the member considers [his/her] | (Need for) Happiness | Affected by Spirituality/ Neuroticism; Realism; Balance; |

TABLE I-continued

| DOMAIN & Sub-Domain | USER STATE/TRAIT | DEFINITION | MOTIVATOR | CONDITIONS AFFECTING |
|---|---|---|---|---|
| | | condition in a positive manner, and is confident with [his/her] future - A Low Optimism might reveal the member as apprehensive, even anxious, having the tendency to judge [his/her] current life as not satisfying, and to perceive [his/her] future as extremely uncertain. | | |
| | Emotional Stability | The extent to which the member is calm and tempered most of the time, in control of [his/her] emotions and impulses - A low Emotional Stability might reveal the member as a moody, agitated person, who can easily be prone to stress and experiences unpleasant emotions, such as anger or sadness. | (Need for) Happiness | Affected by Emotion awareness, expression and emotion regulation; Ability to manage stress; Mental state of being; Stillness; Checking in with yourself |

Another algorithm design in the invention provides for determination, based on the user's questionnaire responses, of the difference (represented by the symbol, Δ) between the level of each state of the user and the relative motivational power of the corresponding motivator—as determined across multiple users. To determine Δ therefore, one first determines the motivational power represented by a particular motivational message for users at a variety of levels of the corresponding state-related trait. To determine such motivational power, one sends one or more related motivational messages to the users, and then determines the average (mean) degree by which the state of all users changed in a positive direction, where the greater the degree of such mean change, the larger the Δ value is assigned. The Δ determination can preferably be performed with a deep learning artificial intelligence program.

Thus, once a user's states (and therefore traits) are identified by questionnaire, the messages selected to be sent to him are those which have the highest Δ, and thus, the highest probability of inducing positive changes in traits. Again, the message selection can also be based on additional considerations, such as the particular user's prior responses to a message or similar messages, as well as the user's profile (including, e.g., intelligence, language skills, physical ability).

In addition to providing the messages under the foregoing criterion, other messages are also selected for a user based on the design of their personalized wellness plan. This wellness plan is generated with input from counselors, health professionals, therapists, and others, based on the user's profile. Messages which are necessary to implement and enhance the user's personalized wellness plan may also be sent to the user.

Another aspect of a well-being program is risk segmentation. Patients lacking language skills, or sufficient funds for transportation, optimal medication or organic foods, or who are unlikely to take medications, are in a higher risk of non-compliance with a wellness plan. For some patients, their ability to change negative behaviors or increase positive behaviors are undetermined. Risk segmentation includes determination of the person's social habits and behavior, and their goals, and ultimately, an assessment of the risk of non-compliance with a wellness plan, which can be factored into the message selection algorithms.

The message selection algorithm can also determine the best manners of phrasing and displaying the selected messages on a user's device, to obtain the most positive responses. This phase of message selection is determined using an algorithm which (i) first determines optimal messages from a large number of users, and (ii) then determines which of such messages is most effective in producing positive changes in states for a particular user; based on that user's prior experience with receiving such messages and the user's prior changes in response. In the second phase (ii), the individualized message selection is constantly updated by determining the change-inducing effect of previous messages on the user; and in view of any changes to the user's personalized wellness plan. Each patient is regularly monitored for compliance and progress with respect to his/her personalized wellness plan, and this is factored into the message selection algorithm.

Having quantified the domains and sub-domains for a particular user, the motivator messages can then be grouped, preferably in accordance with the various categories of motivators in Table I. Where one wishes to induce positive change to the greatest degree in a particular trait, one selects and sends messages from the group of motivator messages associated with that particular trait.

In each group of motivator messages, some will have been tested against other user users and shown to be effective, and some will be included in the group without testing; but with the expectation that they can induce positive changes. After sending previously tested messages to a particular user and finding that they do not induce positive changes, one can send further tested messages from the same group, or untested messages from the same group, which have not been tested in other users for effectiveness. Where any message sent results in a positive change in a state for a particular user, one can also send other tested or untested messages in the same group to the user.

DETAILED DESCRIPTION

HSolistic well-being assessments can best be provided using a natural conversational approach, in addition to using multiple choice questionnaires, with graded responses. The patient profile includes well-being topics such as lifestyle, sleep, nutrition, alcohol and drug use, and physical activity are explored through evidence-based assessments. Additional situational details, such as patient preferences in food, exercise, activity, rest, and therapy; as well as goals, challenges, values and psychosocial attributes are also evaluated. Some determinations of patient state may be indicated by voice pitch, speech patterns, tics, movements and visual cues, and these may be monitored to add understanding of the patient's situation. Speech and observable information can be assessed and transmitted to a server, or stored locally on a user's microprocessor device.

Such conversations are aided by building trustworthy long-term relationships, with active support available at any time, every day. Primary care providers (PCPs) seek to know their patients, but need active systems to reach that goal.

Evaluating all these factors in the profile and well-being assessment produces the behavior tendency, the mental state/situation, and directs selection of behavior change motivators and determination of the optimal personalized wellness plan, and treatment path. Increased engagement in individuals' health can also address otherwise unmet psychosocial needs. The wellness provider can make recommendations based on the interview and test results, and can add "like" or "don't like" or a graded rating (e.g., of 1 to 5) on the accuracy of the indicated insight based on the test and interview. From there, recommendations based on the interview, test results and rating are developed. The combined data set will be used to form the base data used to create a patient profile and insights; a personalized wellness plan; and which is then used to determine the behavior change motivators and the optimal treatment path. Increasing well-being can generate improved outcomes for patients with chronic conditions or advanced illnesses, as well as those who are otherwise healthy, because, among other reasons, it can increase the likelihood they will follow their medical regimen and drug dosing schedules.

A well-being trait is perceived, and is dependent on the individual's actual state, but not necessarily the same as the actual state. It is best assessed through use of questionnaires, which allow for graded levels of responses: such as strongly agree; agree; disagree; strongly disagree; which allow the user to effectively weight the importance of different domains and traits of the overall well-being assessment to himself, and allow the system to determine where motivators are needed to change states/traits, and to select particular motivator messages most likely to be effective in effecting such change.

Referring to Table I above, exemplary questions to aid in determining the domain "PHYSICAL" and the sub-domain "Functional status," would include:
 a. Has physical pain prevented you from doing something you wanted to do?
 b. Can you walk to the bathroom yourself? To the grocery store?
 c. Can you concentrate enough to review your bank statements and finances?
 d. Do you prefer playing games, crossword puzzles or sitting activities, like watching TV?

An exemplary questions to aid in determining the domain "EMOTIONAL" and the sub-domain "Emotional Stability," would include: "how often, in the past few weeks or months, did you feel happy"?

Added questions on a questionnaire for determining the states for a patient within other domains and sub-domains, as well as the motivators, can be readily apprehended from reviewing Table I and forming questions based on the categories and comments in it. It is also noted that the "DEFINITION" and "CONDITIONS AFFECTING" columns in Table I include queries and definitions relevant to patient state, which can be used directly or with minor modification to guide in selecting questions for the questionnaire. For example, to form questions to determine the Physical, Health (Condition) status, the questions relate to determining (from the "CONDITIONS AFFECTING" column): physical well-being (disease status), nutrition (habits and laboratory analysis of blood chemistry), drug therapy (pharmaceuticals consumed), environment; exercise; and rest/sleep.

The first step in message selection is establishing, initially, a testing a set of messages for each domain, and verifying that the messages are not confusing or ambiguous or difficult to understand and correctly answer, by determining Cronbach's Alphas for a set of messages sent to users. For a quantity which is a sum of K components (also called testlets or items) $X=Y_1+Y_2+Y_3 \ldots Y_K$, Cronbach's alpha is defined as:

$$\alpha = \frac{K}{K-1}\left(1 - \frac{\sum_{i=1}^{K}\sigma_{Y_i}^2}{\sigma_X^2}\right)$$

where $\sigma_X^2$ is the variance of the observed total test scores, and $\sigma_{Y_i}^2$ the variance of component/for the current sample of persons.

To apply Cronbach's alpha in formulating a database of clear questions, for each domain (and sub-domain), one compares the sum of items' variance (through the whole set of responses from test users) to the variance of the sum of the total test scores.

If the sum of items' variance is significantly greater than the variance of the sum of the total test scores, it means that the portion of the errors resulting from misinterpretation, confusion, misunderstanding or related reasons is large, and the dimension the questions are designed to quantify is unreliable.

Table II were the questions posed to a set of 518 test users for the purpose of finding an initial set of questions to quantify the various domains and sub-domains in Table I.

TABLE II

| Domain or Sub-Domain | Questions |
|---|---|
| Health Condition | Over the past months: How many times did you feel you were out of shape? |
| | Over the past months: How often have you been told by a medical authority you were not at your ideal weight? |
| | Over the past months: How often did things such as smoking, alcohol, drugs or medicines interfere in your life? |
| | Over the past months: How often did you sleep well and feel energetic afterwards? |
| | Over the past months: How many times did you feel tired during the day? |
| | Over the past months: How many times did you experience physical pain? |
| Functional Status | Over the past months: How many times did you have a difficulty moving around? |
| | Over the past months: How often were you unable to perform daily housework or personal care? |
| | Over the past months: How many times did you take a walk outside your home? |
| | Over the past months: How often did you perform sitting activities, such as watching TV, listening to radio or playing video games? |
| | Over the past months: How often did you participate in sports or recreational exercises? |
| | Over the past months: How often did you go on errands or shopping by yourself, using eventually some transportation? |
| Socialization Level | Over the past months: How often did you participate in conversations with people you know? |
| | Over the past months: How many times did you see your family? |
| | Over the past months: How often did you engage in conversation with new people? |
| | Over the past months: How many times did you engage in social activities? |
| | Over the past months: How often did you spend time alone? |
| | Over the past months: How many times did you meet with your friends? |
| Moral Support | Over the past months: How many times did you feel loved and reassured by your relatives? |
| | Over the past months: How often did you share your joys and sorrows with your friends or family? |
| | Over the past months: How often could you count on your relatives when things went wrong? |
| | Over the past months: How often were you able to talk about your problems with your relatives? |
| | Over the past months: How many times did you feel misunderstood by those that count for you? |
| | Over the past months: How many times did your relatives listen to and understand your concerns? |
| Self-Esteem | Over the past months: How many times did you feel proud of yourself? |
| | Over the past months: How many times did personal criticisms affect you? |
| | Over the past months: How often did you think that others were more successful than you? |
| | Over the past months: How often did you trust yourself to succeed in a difficult situation? |
| | Over the past months: How many times did you feel ashamed or humiliated in front of others? |
| | Over the past months: How often have your abilities been recognized by others? |
| Sense of Achievement | Over the past months: How often did you schedule tasks or activities in order to achieve a bigger purpose? |
| | Over the past months: How many times did you set challenging goals for yourself? |
| | Over the past months: How often did the things you do in your daily life make clear sense to you? |
| | Over the past months: How often did you feel a sense of accomplishment for what you did? |
| | Over the past months: How many times did you do something meaningful for you? |

TABLE II-continued

| Domain or Sub-Domain | Questions |
|---|---|
| | Over the past months: How often did you have difficulty determining your plans and goals in life? |
| Life Enjoyment | Over the past months: How many times did you do something you enjoy? |
| | Over the past months: How often did you feel bored while doing something? |
| | Over the past months: How many times did you laugh out loud with other people? |
| | Over the past months: How often were you entertained by learning new things or discovering new places? |
| | Over the past months: How many times did you find your daily life to be interesting? |
| | Over the past months: How often did you consider your daily life to be a dull routine? |
| Life Stability | Over the past months: How often has it been difficult to pay for necessary life expenses? |
| | Over the past months: How many times have you experienced a sense of home? |
| | Over the past months: How often did you unwillingly change living places, including workplaces? |
| | Over the past months: How often did you have to sustain yourself with few tangible resources at your disposal? |
| | Over the past months: How many times did you ask for financial support from your family, friends or others in your social circle? |
| | Over the past months: How often did you consider your living conditions to be reliable enough? |
| Optimism | Over the past months: How often have you been concerned about the future? |
| | Over the past months: How many times did you look at the bright side of your situation? |
| | Over the past months: How many times did you expect things to go your way? |
| | Over the past months: How many times did you fear the worst in an uncertain situation? |
| | Over the past months: How often did you find the positive in a difficult situation? |
| | Over the past months: How often did you feel you would surely recover from your problems? |
| Emotional Stability | Over the past months: How many times did you remain calm under pressure? |
| | Over the past months: How many times did you feel completely relaxed? |
| | Over the past months: How often did you get irritated when things differed from what you wanted? |
| | Over the past months: How often did you feel your emotions were out of control? |
| | Over the past months: How often did you get overwhelmed with stress? |
| | Over the past months: How many times did you do or say things on impulse? |
| Need for Energy | At the present time: How important is it to you to improve your strength and stamina? |
| | At the present time: How important is it for you to eat healthier? |
| | At the present time: How important is it for you to feel refreshed when you wake up? |
| | At the present time: How important is it for you to get in better physical shape? |
| | At the present time: How important is it to you to feel more active during the day? |
| | At the present time: How important is it for you to have greater control of your fitness? |
| Need for Mobility | At the present time: How important is it to you to improve your mobility and freedom of action? |
| | At the present time: How important is it for you to participate in sports or recreational exercises? |
| | At the present time: How important is it for you to have easy access to transportation? |
| | At the present time: How important is it to you to go outside? |
| | At the present time: How important is it for you to travel around independently? |
| | At the present time: How important is it to you to do outdoor activities? |
| Need for Social Interactions | At the present time: How important is it for you to make new acquaintances? |
| | At the present time: How important is it to you to participate in social activities? |
| | At the present time: How important is it for you to have multiple social interactions during the day? |
| | At the present time: How important is it for you to stay connected with people you have just met? |
| | At the present time: How important is it for you to frequently see your relatives? |

TABLE II-continued

| Domain or Sub-Domain | Questions |
|---|---|
| | At the present time: How important is it to you to get along with everybody in your surroundings? |
| Need for Meaningful Relationships | At the present time: How important is it for you to be able to count on friends or family in tough situations or emergencies? |
| | At the present time: How important is it for you to develop and nurture deep relationships with people you like? |
| | At the present time: How important is it for you to feel listened to and understood by people you know well? |
| | At the present time: How important is it for you to be able to confide in your relatives? |
| | At the present time: How important is it for you to feel loved by your relatives? |
| | At the present time: How important is it to you to receive help and moral support from relatives when you got in trouble? |
| Need for Recognition | At the present time: How important is it for you to see your abilities acknowledged by others? |
| | At the present time: How important is it for you to have the respect of others regarding what you do for them? |
| | At the present time: How important is it to you to receive praise from your relatives when you have accomplished something hard? |
| | At the present time: How important is it for you to be admired by others? |
| | At the present time: How important is it for you that others believe in you? |
| | At the present time: How important is it to you to receive congratulations from others for your efforts? |
| Need for Significant Goals | At the present time: How important is it to you to take on personal challenges? |
| | At the present time: How important is it for you to be able to contribute to big, collective goals, such as doing good for others or for the planet? |
| | At the present time: How important is it for you to have more meaningful personal goals in life? |
| | At the present time: How important is it for you to feel a sense of personal accomplishment on a regular basis? |
| | At the present time: How important is it to you to plan daily activities that fit with your life goals? |
| | At the present time: How important is it for to you to feel in control of your life, with clear goals to achieve? |
| Need for Fun | At the present time: How important is it to you to feel cheerful when doing something? |
| | At the present time: How important is it for you to have fun when interacting with others? |
| | At the present time: How important is it for you to have exciting experiences? |
| | At the present time: How important is it for you to feel entertained on a regular basis? |
| | At the present time: How important is it for you to have your daily life filled with activities that interest you? |
| | At the present time: How important is it to you to achieve things just for fun? |
| Need for Security | At the present time: How important is it to you to have back-up plans when undertaking something? |
| | At the present time: How important is it for you to have a sense of home? |
| | At the present time: How important is it for you to have a comfortable budget? |
| | At the present time: How important is it to you to be financially independent? |
| | At the present time: How important is it for you to have more material wealth at your disposal? |
| | At the present time: How important is it for you to have more stable living conditions? |

Cronbach's Alphas are considered to indicate a reliable set of questions when they are >0.7 for a domain. For the domains and sub-domains in Table II, only the first three (functional status, moral support, need for security) showed Cronbach's Alphas of less than 7; all the other domains were greater than 7, and thus all those questions can be considered initially reliable, and used to quantify the associated domains and sub-domains for users.

Having established the status of the traits, weighting of responses to particular questions can also be beneficial in diagnosis and message selection. Weighting can be carried out by an algorithm by the server. This may be a needed step is responses to certain questions indicate deviations from desired traits, when in fact the deviation is less or more than indicated. Where such variations are identified (which can be carried out by a Deep Learning AI program across a broad population) the responses to the questions can be weighted by the server to arrive at a more accurate picture of the actual level of the state/trait in question.

Among the important bases of the system, is a relationship between the user and a wellness provider, who makes initial contact with the user, assists in completing the user's personal profile (used later for identification) and works through the queries in the initial questionnaire. This information is used to prepare the patient's personalized wellness plan, and to monitor progress in the implementing the plan and the user's well-being. This information, including the progress, is preferably presented by the server in graphical form. The wellness provider is available to listen, collaborate, and encourage throughout the process and the implementation of the plan.

The wellness provider also suggests and makes referrals such as to emergency or urgent hospital care, medical specialists, mental health and community services, as well as other local resources, including, for example, another wellness provider.

A function for the wellness provider can include assessing the reliability of responses from each user. The reliability of the responses is affected by, for example, the user's communication style (dominance versus need to influence); the user's conflict management style (self-esteem versus need for competition); and, the user's decision-making style (perspective versus need for autonomy).

To assess the reliability of responses from each user, the wellness provider must also assess the user's historical behavior, and responses to prior motivational messages or provider suggestions.

The wellness provider must also assess the user's instant situation, by determining, for example, whether at the interview the user is present, relaxed, supported, and responds cogently and quickly. Voice and body language can provide added clues on the user's state and situation.

Finally, most importantly, the wellness provider must assess and understand the user's well-being goals and aspirations. With all this information from a user, the A value can be determined and used to form UserMotivator Messages, and/or the user's traits can be provided weights again; based on the wellness provider's input into the actual state of the user's traits; which is based on adjusting for the reliability of the responses as above.

Figure 1A:
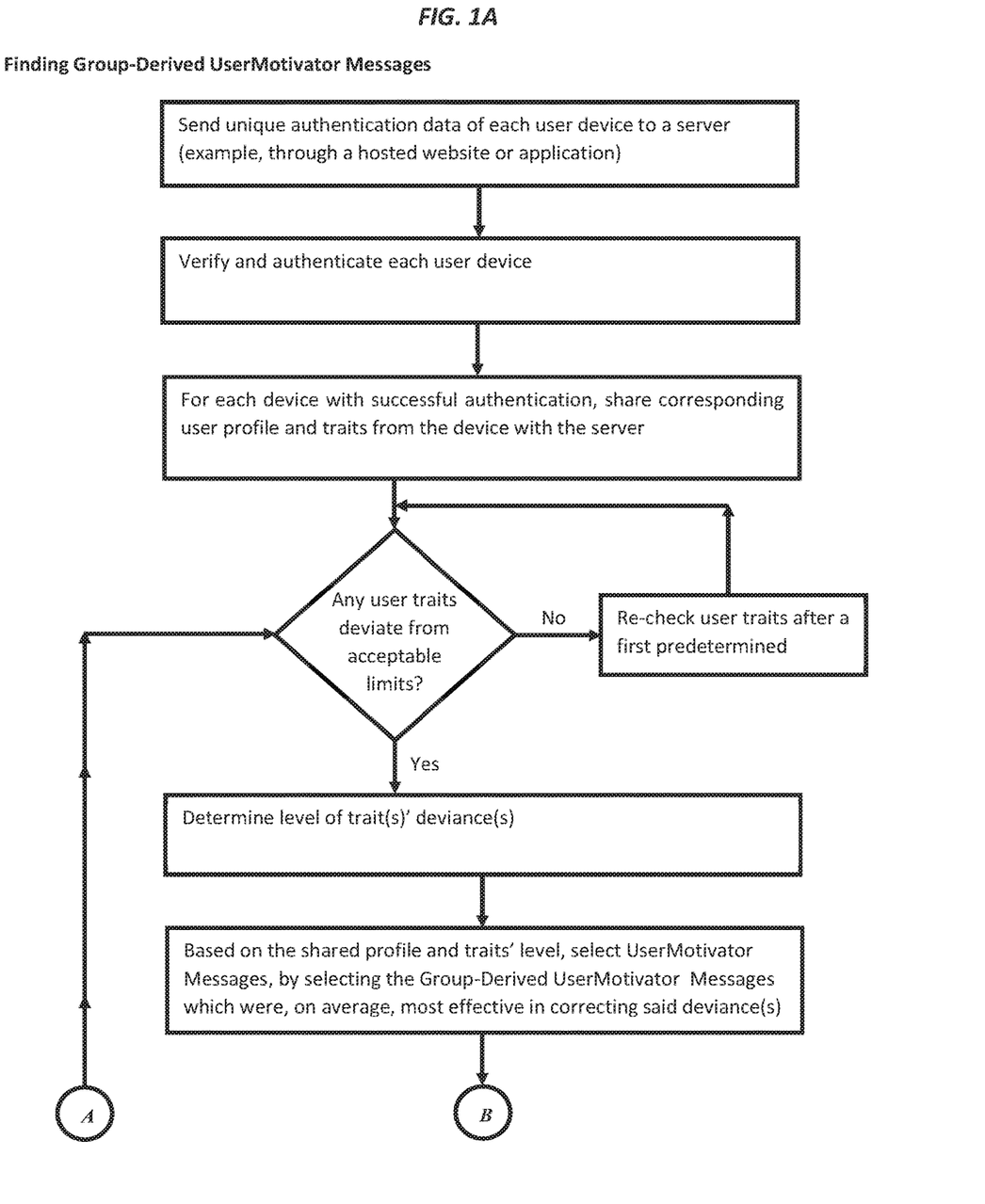
FIG. 1A is the first page of a flow chart depicting a first step in message selection for an individual user, based on responses from a group of users.
Figure 1B:
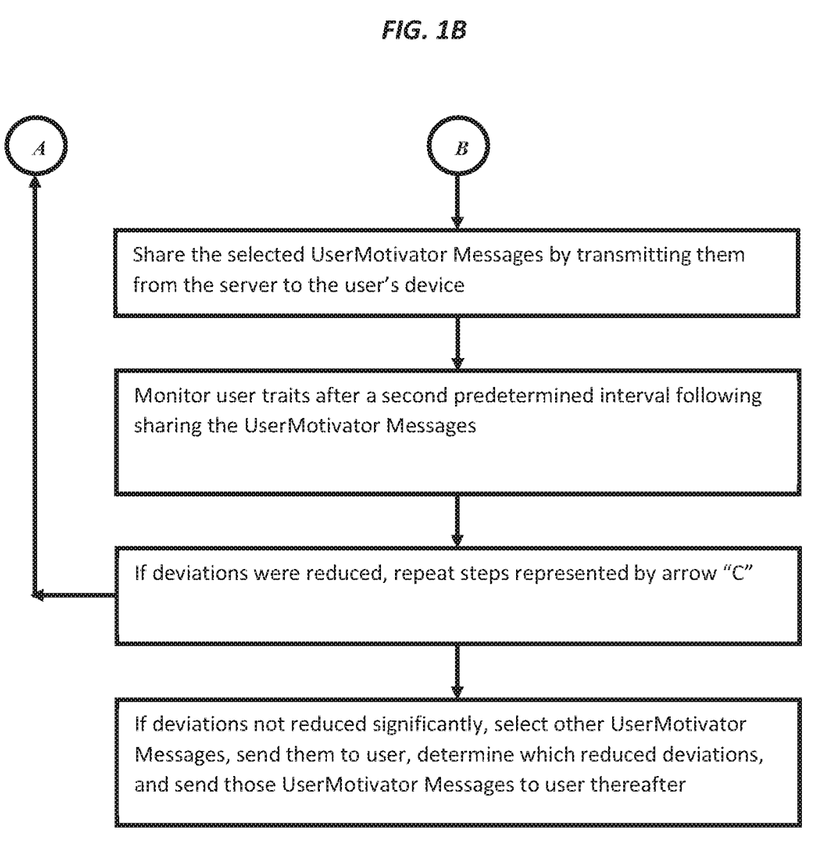
FIG. 1B is the second page of the flow chart of FIG. 1A.

FIGS. 1A, 1B show the server analyzing UserState and determining UserMotivator Messages. UserMotivator Messages are designed by analysis of data from Other Users' Devices, where the server uses an algorithm to determine Group-Derived UserMotivator Messages which induce the most positive change in UserState, averaged across the users, for a variety of levels of UserStates. FIG. 1 uses the term "correcting deviances" as a synonym for "inducing positive change." Again, the level of positive change in UserStates is based on the users' graded responses to a questionnaire, which is sent by the server periodically, following sending of UserMotivator Messages.

Figure 2A:
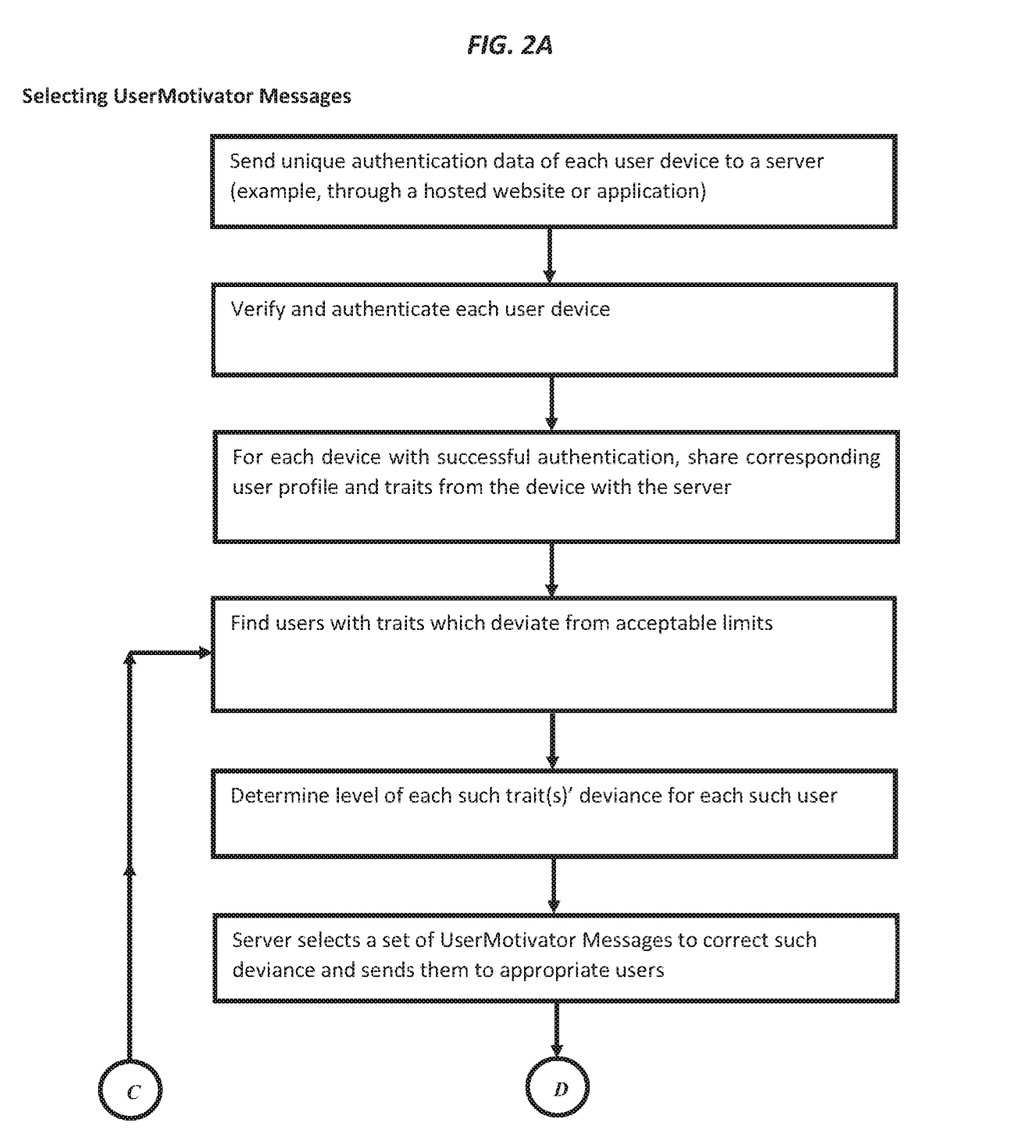
FIG. 2A is the first page of a flow chart depicting message selection for an individual user based on responses from a group of users.
Figure 2B:
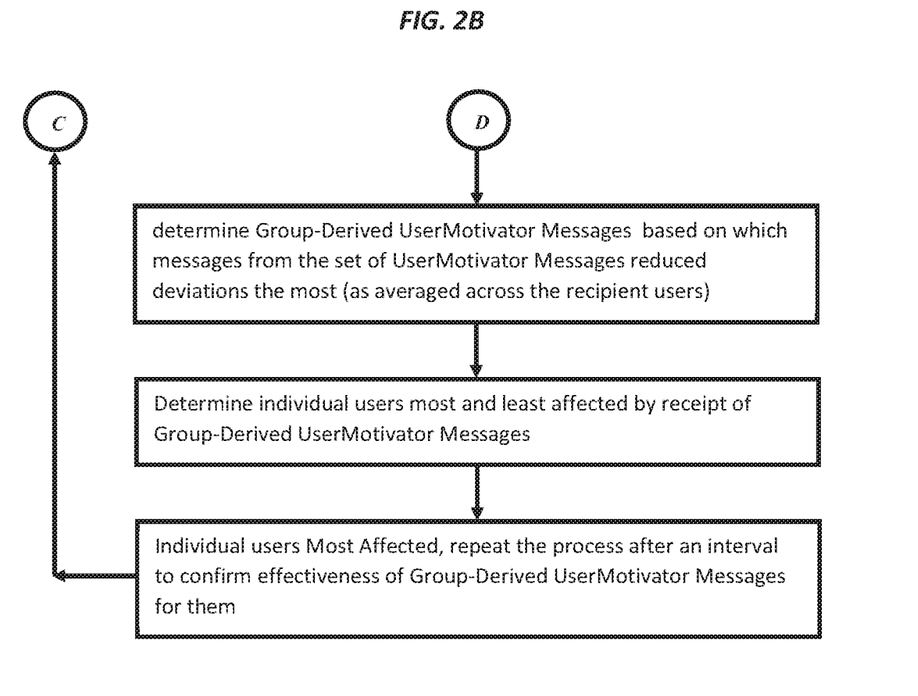
FIG. 2B is the second page of the flow chart of FIG. 2A.

FIGS. 2A, 2B show one user's device interacting with a server, and a website, which selects and sends the user messages designed to most enhance the user's well-being; where the server firsts selects messages by comparing the user profile and deviations in trait levels with appropriate Group-Derived UserMotivator Messages which were most effective for other users (as averaged) and then sending selected Group-Derived UserMotivator Messages to the user. If those selected messages are not effective, other messages particularized for that user are selected, on a personalized basis, some of which may or may not have been sent to and tested on other users. The user's states in response to certain messages is determined by the user entering graded responses to a questionnaire, where the questionnaire is preferably sent by the server to the user periodically; and completed and returned.

For an individual user with significant deviations from optimal in levels of UserStates, he is sent one or more of the motivator messages associated with producing positive changes in those states (reducing the deviation of the level of those UserStates). He is then sent another questionnaire to determine if the messages were effective in producing such positive changes in the subject UserState levels. If so, those messages are noted by the system, and the same messages (or variants of them) are subsequently sent if the same traits are scored by the user as more positive in any follow-up questionnaire sent from the server. It is possible to send only personalized (untested on other users) messages to any particular user, or to send a mixture of tested and untested messages. Where tested messages do not produce positive changes in the subject UserState levels, untested messages are preferably selected.

The invention includes a wireless network, deploying a health and well-being program that connects a wellness professional with users (especially older users). Such a system uses questionnaires to determine a number of benefits and characteristics of users, including: determine what matters to the user; understand personas & values; provide choices; navigate challenges; and, discern social determinants.

The invention also includes analysis of graded questionnaires from a pool of users, which can be performed using AI and deep learning algorithms. This results in a more complete picture of users' well-being, not limited to just disease management. The system's goal is to provide planning and support so that older adults can enhance their well-being while improving disease management.

The questionnaire is used by the server to generate a personalized wellness plan, which is sent to the user's device, and may include one or more of the following suggestions for the user:

Relationship advice: get out more; talk to your family on the phone; download senior singles app;

Activities: go outside to the park, go shopping, cook your food;

Rest: lie on bed and sleep, engage in relaxation and/or meditation;

Medication: take all meds recommended; indicate why if any meds are not consumed;

Diet: eat first/second/third meal now; indicate why if any foods recommended are not consumed;

Physical and Mental Exercise: go to gym now; perform the following routines; indicate why if any recommended activities are not performed; and Physio-Therapy and Mental-Therapy: go to appointments now; if not attending a session, or not performing any recommended actions, indicate why.

The invention includes a website which provides identification of users attempting to input information, and instructs them on how to submit completed questionnaires, and where to find blank questionnaires for use. The website also provides a look-through function to allow direct contact by users with health professionals, hospitals and care facilities, wellness service providers and other resources. The website preferably also locates users (through the GPS function on their devices) and sends information about proximal health professionals, hospitals and care facilities, wellness service providers and other resources.

The invention also includes a server which has its functioning altered for analysis of large data sets, in particular, the questionnaire responses input by a large number of users, which are then used to determine the median response to particular motivational messages sent to the users, and the relative proportion of each other response; all of which is used to determine the degree of deviation in each of a user's state/trait from the normal or optimal state/trait. The invention also includes a server which has its functioning altered for analysis and tracking of an individual user's response to particular motivational messages, to aid in determining which messages to send to such user.

UserMotivator Messages can be readily determined from the "DEFINITIONS" and "CONDITIONS AFFECTING" columns of Table I. For example, UserMotivator Messages for the SOCIAL domain, and the "Connectedness/Socialization level" sub-domain, where the definition is related to the number of regular interactions with people, include:

Attend social activities you enjoy such as dance or exercise classes;
Spend time with family members and friends;
Attend to your pets' needs; and
Attend professional conferences, and author of a paper or seek positions as speaker.

UserMotivator Messages for the EMOTIONAL domain, and the Optimism sub-domain, might include:

Attend your church services and related activities;
Read medical literature about your diseases and conditions;
Seek medical professional discussions about your diseases and conditions;
Read novels and watch movies with an optimistic message.

UserMotivator Messages for the SENSE OF SELF domain, and the Self-Esteem sub-domain, might include:

Sometimes you may not feel like it, but there is a purpose for you.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of improving a user's well-being in an interactive system, comprising:
  a. querying a group of users to determine each user's identifier profile and relative levels of a number of state-related traits, and identifying traits for each user for which said relative levels deviate significantly from optimal;
  b. sending the users' identifier profile and said relative levels from a device controlled by the users to a website controlled by a server;
  c. identifying the users by the website and providing said relative levels to the server;
  d. selecting, by the server, motivational messages from a group of messages likely to reduce said deviations in said relative levels based on finding a value >0.7 of Cronbach's Alpha for the set of motivational messages, x, wherein each users responses to the motivational messages are scored, and wherein the Cronbach's Alpha value is:

$$\alpha = \left(\frac{k}{k-1}\right)\left(1 - \frac{\sum_{i=1}^{k}\sigma_{y_i}^2}{\sigma_x^2}\right)$$

where $\sigma^2 x$ is the variance of the observed total scores from users and where $\sigma^2_{y_i}$ is the variant of component i for the responding users;
  e. sending the selected motivational messages to the devices controlled by the users;
  f. querying the users by sending a questionnaire from the server to said device, to determine if said deviations were reduced;
  g. determining a subset of the selected motivational messages which reduce the deviation by greater amounts than others, where the amount of said deviation reduction is the average of all users reduction in deviation following receipt of said selected motivational messages; and
  h. sending said subset of selected motivational messages to another user whose relative levels deviate significantly from optimal.

2. The method of claim 1 wherein if sending said subset of selected motivational messages to the other user does not reduce said deviation for said other user, selecting and sending additional but different motivational messages from said subset to said user.

3. The method of claim 1 wherein if sending said subset of selected motivational messages to the other user does not reduce said deviation for said other user, selecting and sending motivational messages from said group of messages which have not been previously sent to said other user.

4. The method of claim 2 wherein if sending the additional but different motivational messages reduces said deviations for said user, sending them again and/or sending other messages from the same group as the additional but different motivational messages to said other user.

5. The method of claim 3 wherein if sending the motivational messages from said group of messages which have not been previously sent to said other user reduces said deviations for said user, sending them again and/or sending other messages from the same group to said other user.

6. The method of claim 1 wherein the querying in part a is performed by a wellness provider.

7. The method of claim 1 wherein the querying in part a further includes questioning the user about his/her diseases or conditions.

8. The method of claim 1 wherein the querying in part a further includes determining user preferences for food, exercise, activity, rest, and therapy.

9. The method of claim 1 wherein tested motivational messages are those shown most effective on average, for other users to reduce the deviation in the levels of said traits.

* * * * *